(12) United States Patent
Ishikawa et al.

(10) Patent No.: US 7,361,802 B2
(45) Date of Patent: Apr. 22, 2008

(54) DISPOSABLE PULL-ON WEARING ARTICLE

(75) Inventors: Hiroki Ishikawa, Kagawa-ken (JP); Satoru Sakaguchi, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 324 days.

(21) Appl. No.: 10/991,478

(22) Filed: Nov. 19, 2004

(65) Prior Publication Data
US 2005/0113774 A1    May 26, 2005

(30) Foreign Application Priority Data
Nov. 20, 2003   (JP)   ............................... 2003-390290

(51) Int. Cl.
*A61F 13/15*   (2006.01)
(52) U.S. Cl. ............... 604/361; 604/365; 604/367; 604/358.01; 604/366
(58) Field of Classification Search ............... 604/361, 604/366, 367, 385.01, 365, 362, 381, 364; 116/200, 206, 207
See application file for complete search history.

(56) References Cited

U.S. PATENT DOCUMENTS 5,690,624 A * 11/1997 Sasaki et al. ............... 604/361

FOREIGN PATENT DOCUMENTS

| JP | 2002-657    | 1/2002  |
| JP | 2002-153503 | 5/2002  |
| JP | 2002-369841 | 12/2002 |
| JP | 2003-049353 | 2/2003  |
| JP | 2004-298362 | 10/2004 |

* cited by examiner

*Primary Examiner*—Jacqueline F. Stephens
(74) *Attorney, Agent, or Firm*—Lowe Hauptman Ham & Berner LLP

(57) ABSTRACT

In a disposable pull-on wearing article, sheet strips carrying thereon display elements are bonded to an inner surface of an elastically stretchable outer sheet of the article. An inner sheet facing inner surfaces of the sheet strips and being elastically stretchable is bonded to the outer sheet intermittently in a waist-surrounding direction as well as in a vertical direction orthogonal to the waist-surrounding direction in a region extending from lateral edges of sheet strips to spots at which front and rear waist regions of the article are bonded to each other along transversely opposite side margins of the waist regions.

12 Claims, 6 Drawing Sheets

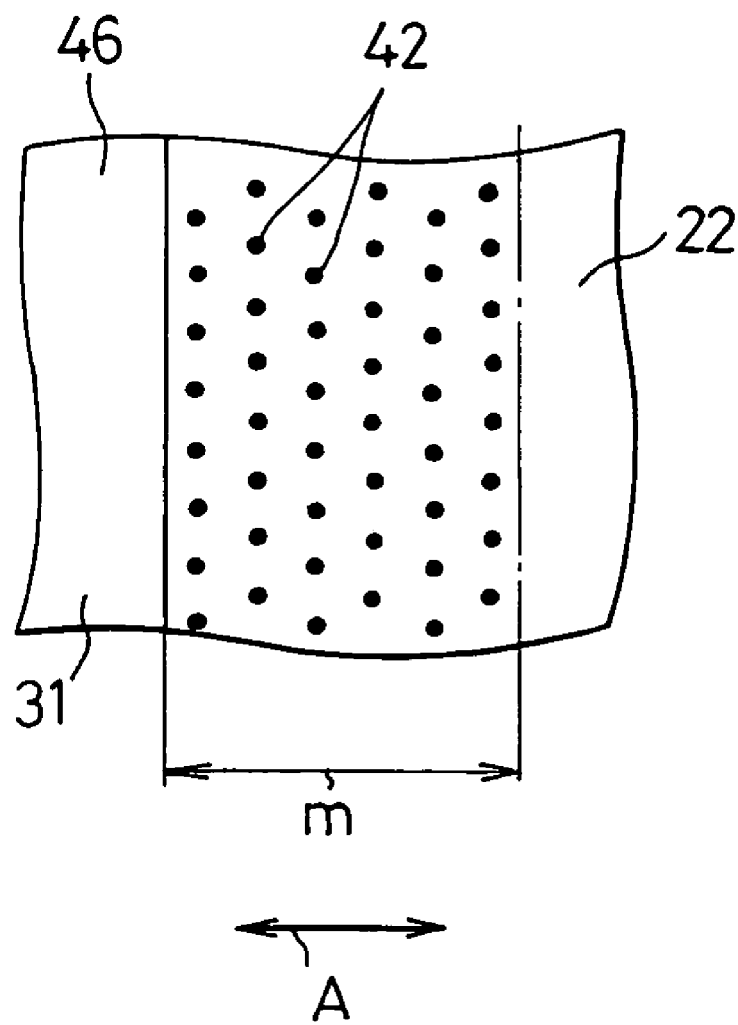

DISPOSABLE PULL-ON WEARING ARTICLE

RELATED APPLICATIONS

The present application is based on, and claims priority from, Japanese Application Number 2003-390290, filed Nov. 20, 2003, the disclosure of which is hereby incorporated by reference herein in its entirety.

BACKGROUND OF THE INVENTION

The present invention relates to disposable pull-on wearing articles such as for example, diapers.

Unexamined Japanese Patent Application Publication No. 2002-153503 (thereinafter referred to as "Citation 1") discloses a disposable diaper including a backsheet made of light transmissive plastic film and an indicator means adapted to be visually recognized from the outside of the backsheet.

Unexamined Japanese Patent Application Publication No. 2002-657 (hereinafter referred to as "Citation 2") discloses a pull-on disposable diaper having a backsheet comprising a film printed on its outer surface with an image and a nonwoven fabric laminated on the outer surface of the film wherein the nonwoven fabric has a light transmission in a range of 40 to 83%.

For the diaper disclosed in Citation 1, the backsheet preferably comprises a plastic film having a sufficiently high light transmission to facilitate the indicator means to be visually recognized from the outside of the backsheet and an appropriate light diffusivity to prevent the body liquid absorbent core lying inside the backsheet from seen through the backsheet. However, the plastic film meeting such requirements may often result in an unacceptably thin film which may be readily broken.

For the diaper disclosed in Citation 2, in order that the image can be seen clearly from the outside of the backsheet, the nonwoven fabric preferably has a sufficiently small basis weight to improve the light transmission of the nonwoven fabric. However, such nonwoven fabric also may result in an unacceptably thin nonwoven fabric which may be readily broken.

As the backsheet for the diaper disclosed in Citation 1 or Citation 2, it is well known to use an elastically stretchable nonwoven fabric or a plastic film made of plastic elastomer or an elastically stretchable nonwoven fabric made of crimped fibers. However, the nonwoven fabric or the plastic film made of plastic elastomer generally has a relatively low light transmission. In such a case, to facilitate the display element such as indicator means or image to be visually recognized from the outside of the backsheet, a film printed with the display element is preferably bonded to the inner surface of the backsheet as thin as possible by means of adhesive or heat-sealing technique. However, such backsheet is disadvantageous in that the region in which the film has been bonded to the backsheet may be affected by a stress concentrating in this region and be broken therein as the backsheet is stretched in a waist-surrounding direction. The backsheet formed from a nonwoven fabric made of crimped fibers inevitably become bulky and, in order to facilitate the display element to be visually recognized from the outside of such backsheet, it is preferred to use the backsheet as thin as possible. However, in this case also, the backsheet is apt to be broken in the region thereof in which the film printed with the indicator element has been bonded to the backsheet.

SUMMARY OF THE INVENTION

It is an object of the present invention to provide a disposable pull-on wearing article comprising a sheet strip formed with a display element such as an indicator means is bonded to an inner surface of an elastically stretchable sheet so improved to facilitate the display element to be visually recognized from the outside of this elastic sheet without an anxiety that the elastic sheet might be readily broken even if the elastic sheet is repeatedly stretched and contracted.

The present invention is directed to a disposable pull-on wearing article comprising a front waist region, a rear waist region and a crotch region, the front and rear waist regions respectively having transversely opposite side margins bonded together so that the front and rear waist regions and crotch region cooperatly define a pants-shaped configuration. The front and rear waist regions include a first sheet which is elastically stretchable in a waist-surrounding direction and the first sheet in at least one of the front and rear waist regions is provided on an inner surface thereof with a display element adapted to be visually recognized from an outside of the first sheet.

The article according to the present invention further comprises the display element being formed on a sheet strip bonded to an inner surface of the a first sheet by means of a first bonding means, the sheet strip being interposed between the first sheet and a second sheet lying inside the wearing article behind the sheet strip and being elastically stretchable in a waist-surrounding direction and the first sheet being bonded to the second sheet by means of a second bonding means in a region extending in the waist-surrounding direction from side edges of the sheet strip to spots at which the transversely opposite side margins of the front and rear waist regions are bonded together, and the second bonding means forming a plurality of bonding spots at which the first sheet and the second sheet being bonded to each other intermittently in the waist-surrounding direction as well as in a vertical direction of the wearing article orthogonal to the waist-surrounding direction. The wearing article according to this embodiment is advantageous in that a stretch stress generated as the first and second sheets are stretched in the waist-surrounding direction can disperse into a plurality of bonding spots formed outside of the side edges of the sheet strip and therefore it is unlikely that the first sheet might be readily broken due to repeated stretch and contract even if the first sheet is relatively thin.

A plurality of the bonding spots are distributed so that the area ratio of these bonding spots per unit area of the inner surface is gradually reduced in the waist-surrounding direction away from the side edges of the sheet strip. The wearing article according to this embodiment is advantageous in that a stiffness of the first sheet which otherwise would become higher due to the presence of the bonding spots is gradually reduced in the waist-surrounding direction and therefore the first sheet can be maintained flexible.

The bonding spots are formed only in a region defined within a range of about 10 to about 50 mm from the side edges of the sheet strip. By gradually reducing the area ratio of the bonding spots in the range as has been described, the first sheet can be protected from breakage due to repeated stretch and contract.

The first sheet and the second sheet are formed from nonwoven fabric layers and a basis weight of the first sheet is a smaller than a basis weight of the second sheet and wherein the first sheet has a luminous transmission of at least 55%. The basis weight of the first sheet is preferably smaller than the basis weight of the second sheet and the first sheet is preferably made sufficiently thin to ensure the luminous transmission of at least 55% in order that the display element can be clearly recognized.

At least one of the first sheet and the second sheet contains elastomer fibers. When both the first sheet and the second sheet are formed from nonwoven fabric layers, component fibers of the respective layers are firmly entangled one with another in the regions where the layers are put flat together and the first sheet integrated with the second sheet in this manner is well resistant to breakage even if the first sheet is relatively thin and, should this integrated sheet be broken, such breakage will not be outstanding. When at least one of the two sheets contains elastomer fibers, a friction coefficient will be correspondingly high and the fibers will not easily disentwined. Consequently, the two sheets will neither be easily peeled off from each other nor be readily broken by repeated stretch and contact.

Among the front waist region, the rear waist region and the crotch region, at least the crotch region is provided on the inner surface of the second sheet with a body fluid absorbent panel including a body fluid absorbent core at least partially wrapped with a liquid-pervious sheet and a middle region of the body fluid absorbent panel as viewed in a transverse direction of the wearing article is bonded to the second sheet and side regions of the body fluid absorbent panel as viewed in the transverse direction of the wearing article is let free from the second sheet. The wearing article according to this embodiment is free from an anxiety that the second sheet might be prevented by the presence of the body fluid absorbent panel from being elastically stretched.

BRIEF DESCRIPTION OF THE DRAWINGS

FIG. 7 is a view similar to FIG. 5.

DETAILED DESCRIPTION OF THE PREFERRED EMBODIMENTS

Details of a disposable pull-on wearing article according to the present invention will be more fully understood from the description of a pull-on diaper as a specific embodiment given hereunder with reference to the accompanying drawings.

Figure 1:
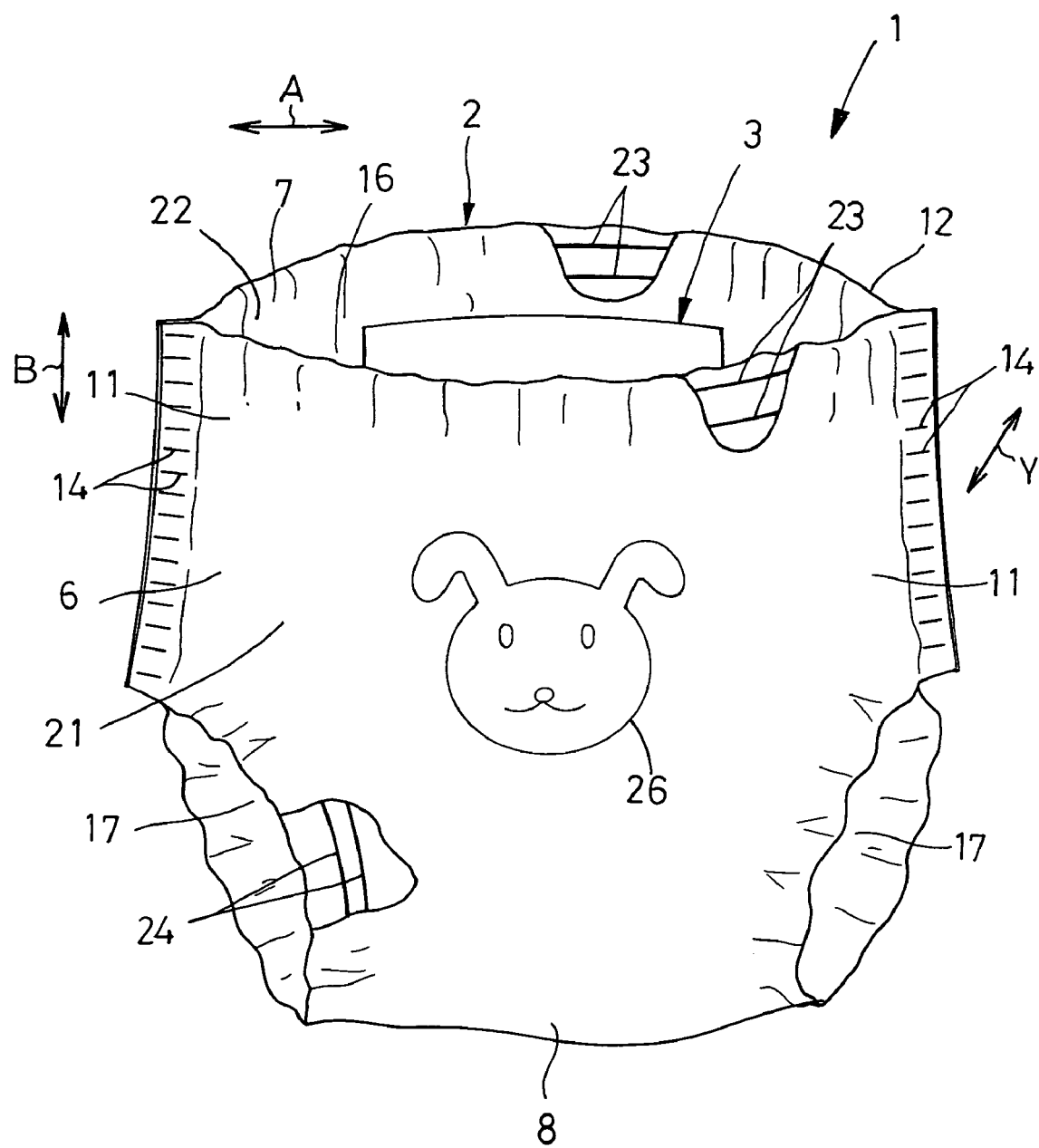
FIG. 1 is a partially cutaway perspective view showing a disposable pull-on diaper as a typical embodiment of the invention.

FIG. 1 is a partially cutaway perspective view showing a disposable pull-on diaper 1. The diaper 1 has a covering chassis 2 and a body fluid absorbent panel 3 attached to the inner surface of the chassis 2. The chassis 2 has a front waist region 6, a rear waist region 7 and a crotch region 8. Transversely opposite side margins 11, 12 of the front and rear waist regions 6, 7 are put flat and bonded together at a plurality of spots 14 intermittently arranged in a vertical direction as viewed in FIG. 1. The chassis 2 further has a waist-hole 16 and a pair of leg-holes 17. Each of the front waist region 6, the rear waist region 7 and the crotch region 8 comprises an outer sheet 21 defining a first sheet facing a wearer's garment (not shown) and an inner sheet 22 defining a second sheet facing the wearer's skin (not shown). Respective peripheral portions of the waist-hole 16 and the leg-holes 17 are provided with a plurality of waist-surrounding elastic members 23 and a plurality of leg-surrounding elastic members 24 both interposed between the outer sheet 21 and the inner sheet 22 and bonded in a stretched state to the inner surface of the outer sheet 21 and/or the inner sheet 22. Through the outer sheet 21 of the front and rear waist regions 6, 7, respectively, images 26 of rabbits are visually recognized from the outside of the diaper 1 (See FIG. 2 also). The image 26 is a display element contributing to various effects. Particularly, the image 26 joyfully decorates the diaper 1, facilitates the front and rear waist regions 6, 7 to be distinguished from each other and conceals the interior of the diaper 1 stained with bodily discharges.

Figure 2:
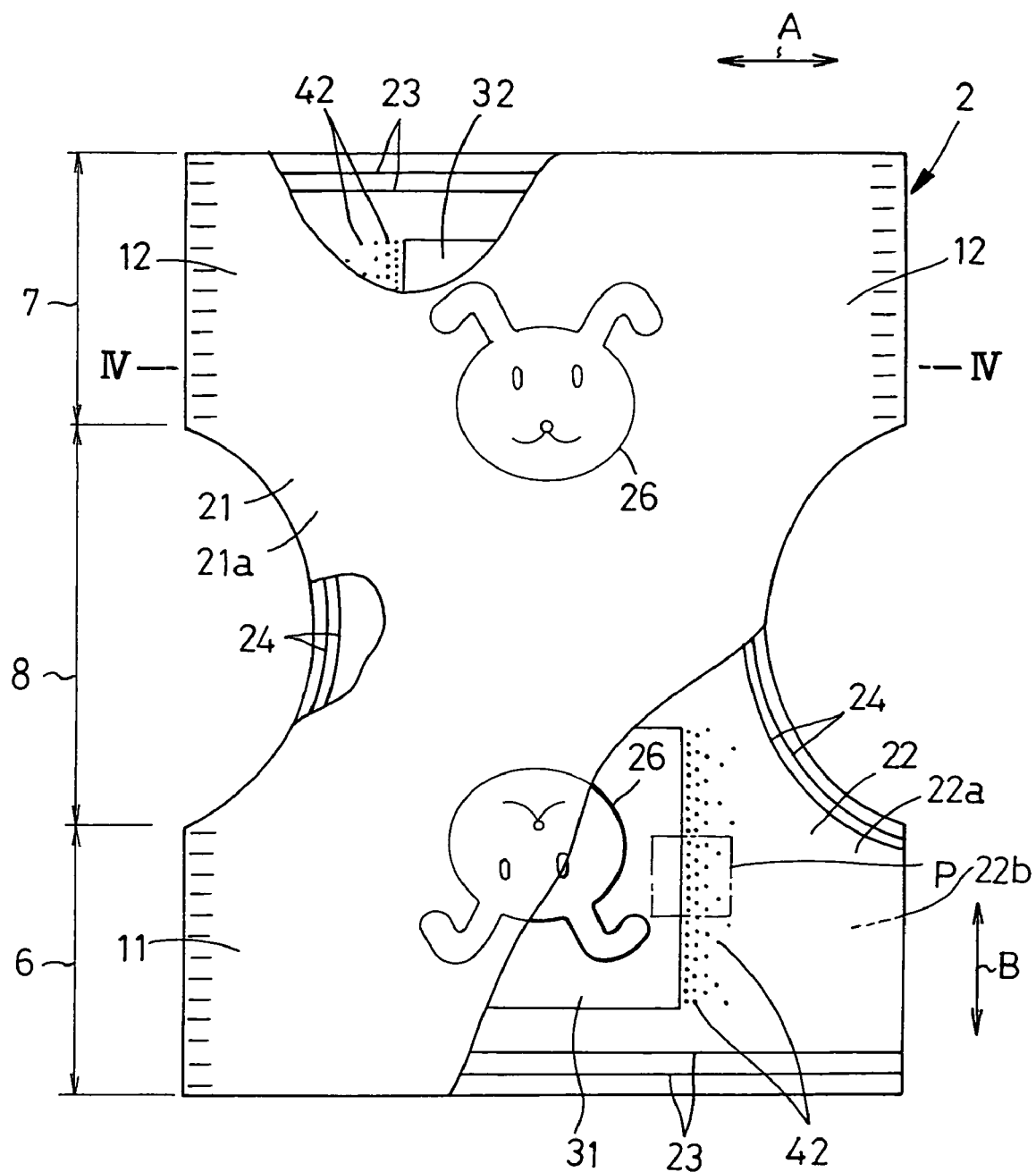
FIG. 2 is a partially cutaway plan view showing the diaper of FIG. 1 as has been developed.
Figure 3:
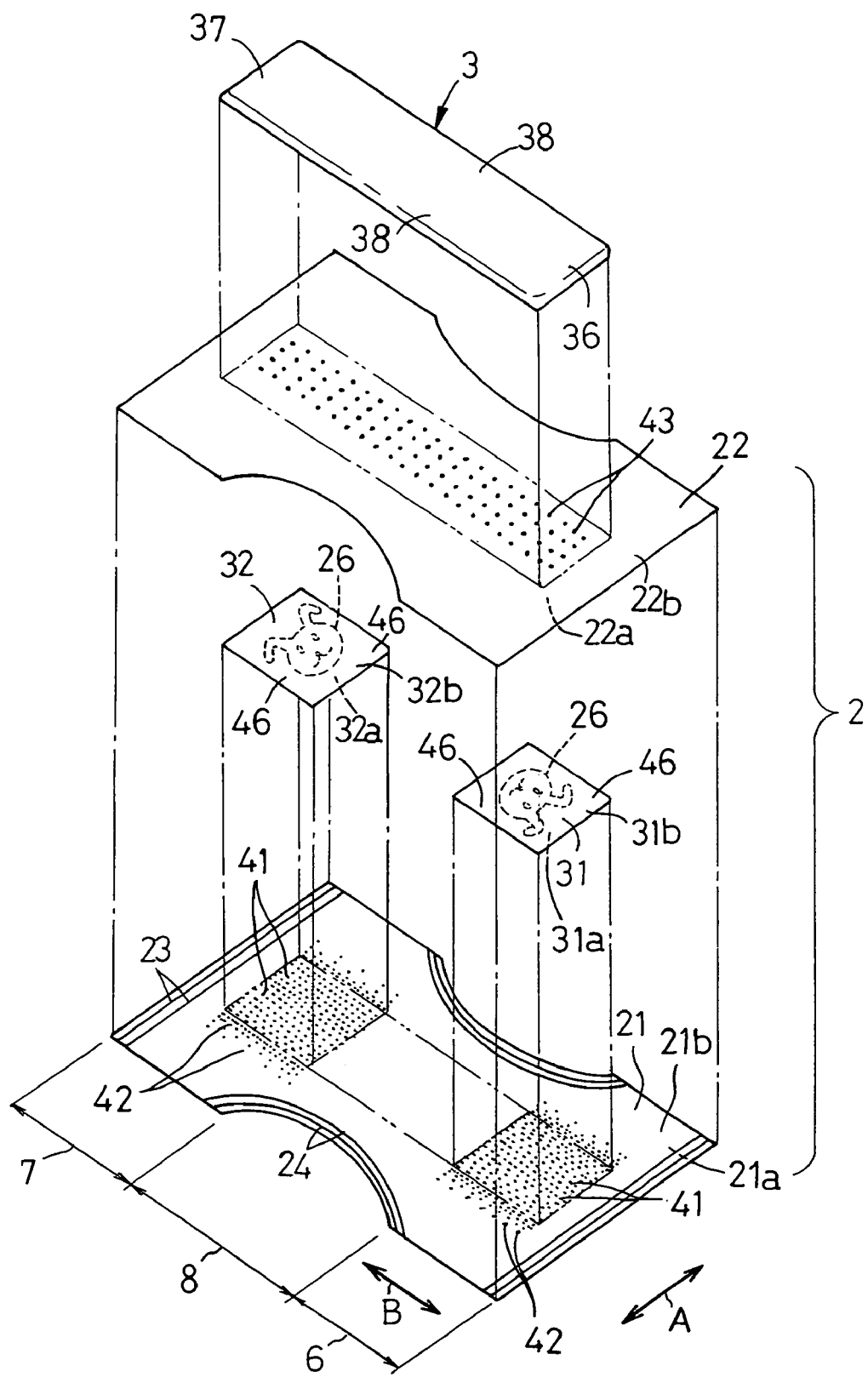
FIG. 3 is an exploded perspective view showing respective components constituting together the diaper of FIG. 2.

The outer sheet 21 and the inner sheet 22 constituting together such chassis 2 of the diaper 1 are respectively formed from sheet materials which are elastically stretchable in a transverse direction A of the diaper 1 and in a vertical direction B orthogonal to the transverse direction A, at least in the transverse direction A. Such sheet material may be selected from the group including a nonwoven fabric of elastic threads made of elastomer, a nonwoven fabric of crimped fibers and elastomer film. The outer sheet 21 and the inner sheet 22 respectively has a generally hourglass-shape and have outer surfaces 21a, 22a and inner surfaces 21b, 22b. In the front and rear waist regions 6, 7, first and second sheet strips 31, 32 printed on respective surfaces facing the inner surface 21b of the outer sheet 21 with the rabbit images 26 are interposed between the outer sheet 21 and the inner sheet 22, respectively. The first and second sheet strips 31, 32 respectively have outer surfaces 31a, 32a and inner surfaces 31b, 32b. Both the first sheet strip 31 and the second sheet strip 32 are dimensioned and placed so that the sheet strips 31, 32 might overlap neither the waist-surrounding elastic members 23 nor the leg-surrounding members 24. Referring to FIG. 2, a portion of the image 26 in the front waist region 6 visible through the outer sheet 21 is indicated by thin lines and the remaining portion of the image 26 printed on the first sheet strip 31 and directly visible because of the outer sheet 21 is partially cutaway is indicated by thick lines. Referring to FIG. 3, the images 26 indicated by chain lines should be understood to be visible from the inner surfaces 31b, 32b of the first and second sheet strips 31, 32 through the sheet strips 31, 32. The first sheet strip 31 and the second sheet strip 32 respectively comprise non-stretchable sheet material to avoid an inconvenience that the images 26 might be distorted as the first and second sheet strips 31, 32 are under a tension. The body fluid absorbent panel 3 is attached to the inner surface 22b of the inner sheet 22 and has a generally rectangular shape extending over the crotch region 8 further into the front and rear waist regions 6, 7. Such body fluid absorbent panel 3 has a front end portion 36 extending across the front waist region 6 in a direction A, a rear end portion 37 extending across the rear waist region 7 in the direction A and transversely opposite side margins 38 extending in a direction B.

FIG. 2 is a partially cutaway plan view showing the diaper 1 of FIG. 1 with the front and rear waist regions 6, 7 having been peeled off from each other at the spots 14 and developed in a back-and-forth direction indicated by double-headed arrow Y and FIG. 3 is an exploded perspective view showing respective components constituting together the diaper of FIG. 2.

Figure 4:
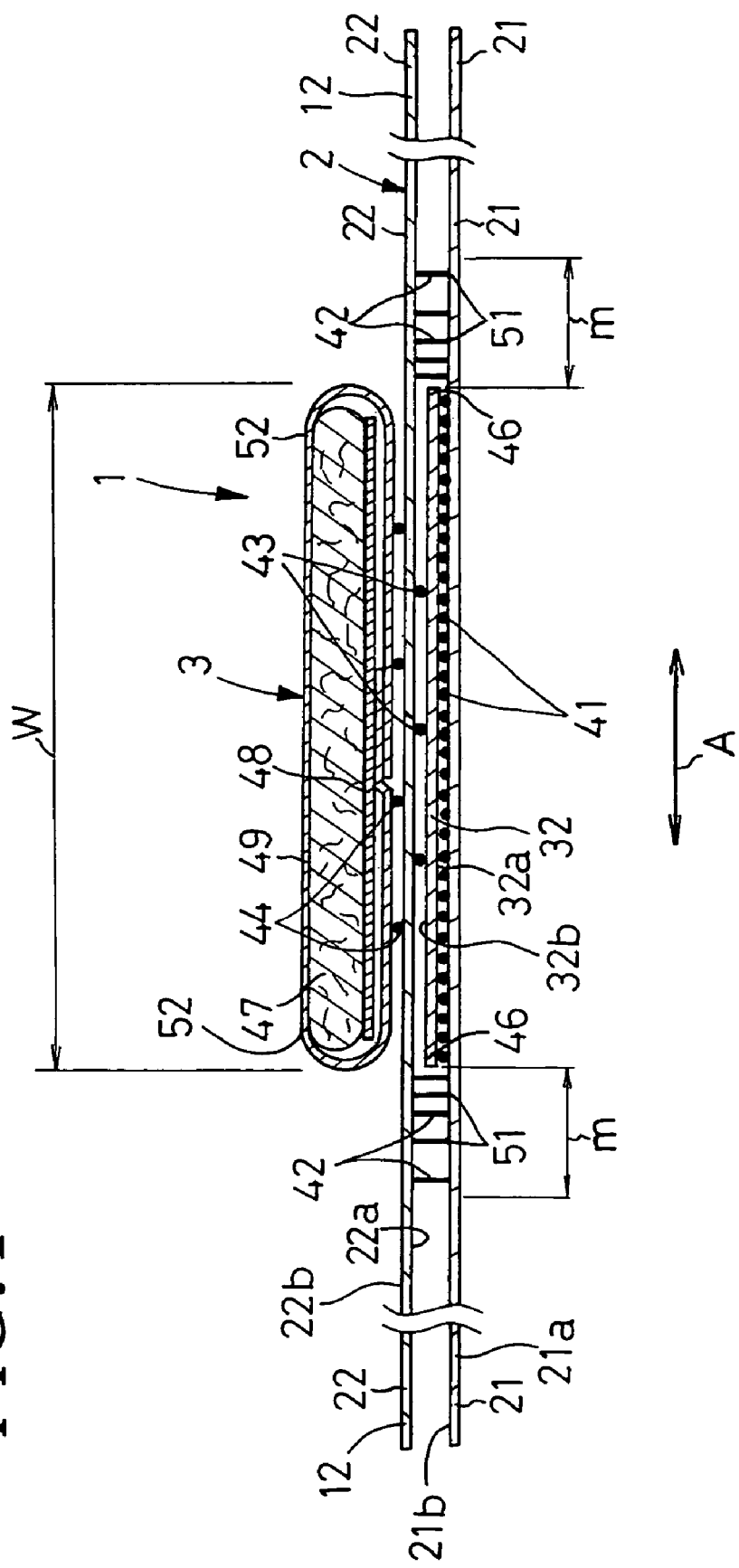
FIG. 4 is a sectional view taken along the line IV-IV in FIG. 2.

FIG. 4 is a sectional view taken along a line IV-IV in FIG. 2, wherein the outer sheet 21, the inner sheet 22, the second sheet strip 32 and the body fluid absorbent panel 3 are illustrated to be spaced apart one from another in the vertical direction in FIG. 4 by exaggerated dimension in order to clarify the presence of first, second, third and fourth adhesive 41, 42, 43, 44. The second sheet strip 32 is bonded to the inner surface 21b of the outer sheet 21 by means of the first adhesive 41 so that the second sheet strip 32 is held in close contact with the inner surface 21b and the image on the second sheet strip 32 may be clearly visible from the outside of the chassis 2. The second sheet strip 32 is bonded also to the outer surface 22a of the inner sheet 22 by means of the third adhesive 43. The outer sheet 21 and the inner sheet 22 define adjustably fixed regions m extending in the waist-surrounding direction from transversely opposite side edges 46 of the second sheet strip 32 to the spots 14 (See FIG. 1) at which the front and rear waist regions 6, 7 are bonded together. More preferably, the adjustable fixed regions m extend from the respective side edges 46 in the waist-surrounding direction by 10 to 50 mm and, only in the adjustably fixed regions m, the outer sheet 21 and the inner sheet 22 are bonded to each other by means of the second adhesive 42. In the chassis 2, portions of the outer sheet 21 and the inner sheet 22 lying along the transversely opposite side margins 12 of the rear waist region 7 are bonded at the spots 14 together with portions of the outer sheet 21 and the inner sheet 22 lying along the transversely opposite side margins 11 of the front waist region 6 as will be apparent from FIG. 1. Such bonding at the spots 14 may be achieved by means selected from the group including sonic welding, heat embossing and adhesion using hot melt adhesive. The inner sheet 22 and the body fluid absorbent panel 3 are bonded to each other by means of the fourth adhesive 44. As will be best understood from the sectional view, the body fluid absorbent panel 3 comprises a body fluid absorbent core 47, a liquid-impervious bottom sheet 48 covering a bottom of the core 47 and a liquid-pervious wrapping sheet 49 wrapping the core 47 and the bottom sheet 48.

In the diaper 1 of FIG. 4, the second sheet strip 32 is coated over its large extent with first adhesive 41 intermittently or continuously in the transverse direction A as well as in the vertical direction B of the diaper 1 so that the image 26 on the second sheet strip 32 may be easily visible. In this case, the region of the second sheet strip 32 occupied by the image 26 and the vicinity thereof may be bonded to the outer sheet 21 but the remaining region may be left free from the outer sheet 21 to avoid an inconvenience that the outer sheet 21 might cause stiff touch over its large extent due to the presence of the first adhesive 41. The region in which the outer sheet 21 and the second sheet strip 32 are bonded to each other is substantially non-stretchable even when the chassis 2 is pulled in the transverse direction A and/or in the vertical direction B since the second sheet strip 32 is non-stretchable. The third adhesive 43 serves to bond the inner sheet 22 to the first sheet strip 31 as well as to the second sheet strip 32 in the front and rear waist regions 6, 7, respectively, and serves to bond the inner sheet 22 to the outer sheet 21 in the crotch region 8. In this way, the region of the inner sheet 22 in which the body fluid absorbent panel 3 is attached to the inner sheet 22 has its strength improved. If such an improvement of the strength is unnecessary, use of the third adhesive 43 may be omitted. The second adhesive 42 is applied on the adjustably fixed region m intermittently in the transverse direction A as well as in the vertical direction B. In the preferred diaper 1, the second adhesive 42 is applied on this adjustably fixed region m in a manner that a coated amount of the second adhesive 42 per unit area of the adjustably fixed region m is gradually reduced from the side edges 46 of the first sheet strip 31 in the transverse direction A (See FIGS. 5 and 6). An area 51 in which the outer sheet 21 and the inner sheet 22 are bonded to each other by means of the second adhesive 42 occupying unit area of the adjustably fixed regions m is also gradually reduced from the side edges 46 in the transverse direction A. In this diaper 1, in the portions extending from the adjustably fixed regions m to the spots 14 arranged along the transversely opposite side margins 11, 12, the outer sheet 21 and the inner sheet 22 are left free from each other, so it is unlikely that the relatively thin outer sheet 21 might present an uncomfortable stiff touch due to the presence of the adhesive. When nonwoven fabric layers are used as the outer sheet 21 and the inner sheet 22, these two sheets placed upon each other in these portions have respective component fibers entangled with one another and can be elastically stretched as in the form of a single nonwoven fabric layer. The outer sheet 21 integrated with the inner sheet 22 in this manner is well resistant to breakage and, should this integrated sheet be broken, such breakage will not be outstanding so far as the breakage occurs in the integrated portions. Particularly when the component fibers contain elastomer, a friction coefficient will be correspondingly high and these fibers will not easily disentwined. Consequently, the two sheets 21, 22 will not be easily peeled off from each other. The fourth adhesive 44 is coated intermittently or continuously in the transverse direction A as well as in the vertical direction B. In the preferred diaper 1, only a middle zone of the body fluid absorbent panel 3 as viewed in the transverse direction A is bonded to the inner sheet 22 by means of the fourth adhesive 44, i.e., transversely opposite side margins 52 of the body fluid absorbent panel 3 are left free from the inner sheet 22. The middle zone of the body fluid absorbent panel 3 bonded to the inner sheet 22 preferably has a width corresponding to about 30 to about 70% of a width W of the body fluid absorbent panel 3. In the diaper 1 of FIG. 1, the front waist region 6 has the same construction as that of the rear waist region 7 shown in FIG. 4.

The outer sheet 21 defining the outer surface of the chassis 2 of the diaper 1 constructed as shown in FIGS. 1 through 4 may be formed using a sheet having a luminous transmission of at least about 55%, preferably of about 70% or higher as measured by "Measuring Method A" in "Luminous Transmission and Total Luminous Reflectance" prescribed in JIS (Japanese Industrial Standard) K 7105 in order to facilitate the rabbit image 26 to be visually recognized from the outside of the chassis 2. The inner sheet 22 lying inside the chassis 2 behind the first and second sheet strips 31, 32 may be formed using a sheet having a thickness allowing the chassis 2 to have a desired tensile strength and to conceal the wearer's skin. In such diaper 1, a stretch stress generated in the outer sheet 21 as the diaper 1 is put on the wearer's body and the chassis 2 is stretched in the transverse direction A disperses into a plurality of bonding spots 51 formed in the adjustably fixed region m. In this course, the portions of the outer sheet 21 and the inner sheet 22 in the adjustably fixed region m can not be stretched at the bonding spots 51 but can be stretched in the transverse direction between each pair of the adjacent bonding spots 51 that are arranged intermittently in the transverse direction. From such viewpoint, the outer sheet 21 and the inner sheet 22 are adjustably fixed to each other in the region m. In the adjustably fixed region m, the area ratio of the bonding spots 51 is gradually reduced from the side edge 46 of the first sheet strip 31 and the second sheet strip 32 in the transverse direction A. Correspondingly it becomes easier for the outer sheet 21 and the inner sheet 22 to be stretched as these sheets 21, 22 get away from the first sheet strip 31 and the second sheet strip 32 and get close to the transversely opposite side margins 11, 12. Such outer sheet 21 is free from an anxiety that the stretch stress might be concentrated into a limited region of the outer sheet 21 which, in turn, might be readily broken from this region.

Stock materials for the outer sheet 21 constituting the chassis 2 may be selected, for example, from the group consisting of a nonwoven fabric made from elastomer fibers having a fineness in a range of about 0.1 to about 8 dtx and crimped conjugate fibers having a fineness in a range of about 0.5 to about 8 dtx both having a basis weight in a range of about 10 to about 100 g/m$^2$, more preferably of about 25 to about 75 g/m$^2$ and a luminous transmission at least of 55%. Stock material for the plastic film constituting the outer sheet 21 may be, for example, elastomer film having a thickness in a range of about 0.01 to about 0.1 nm and a luminous transmission of at least about 55%. It is also possible to use, as the sheet material constituting the outer sheet 21, a composite sheet obtained by laminating an elastically stretchable nonwoven fabric with an elastically stretchable plastic film or a composite sheet obtained by laminating an inelastically stretchable nonwoven fabric or a plastic film with an elastically stretchable nonwoven fabric or a plastic film both having a luminous transmission of at least about 55%, more preferably of about 70% or higher.

Stock materials for the inner sheet 22 may be, for example, from the group consisting of a nonwoven fabric made from elastomer fibers having a fineness in a range of about 0.1 to about 8 dtx or a crimped conjugate fibers having a fineness in a range of about 0.5 to about 8 dtx both having a basis weight in a range of about 18 to about 180 g/m$^2$, more preferably of about 40 to about 100 g/m$^2$. Such nonwoven fabric is preferably sweat-absorbent. Stock materials for the plastic film constituting the inner sheet 22 may be elastomer film having a thickness in a range of about 0.05 to about 0.15 mm. Total basis weight of the inner sheet 22 and the outer sheet 21 is preferably in a range of about 28 to about 280 g/m$^2$, more preferably in a range of 65 to 175 g/m$^2$.

Stock materials for the first sheet strip 31 and the second sheet strip 32 may be selected from various types of a sheet material such as a plastic film, a nonwoven fabric and a paper sheet. Liquid-impervious sheet materials continuously extending over the crotch region 8 further into the front waist region 6 and the rear waist region 7 may be used as the first sheet strip 31 and the second sheet strip 32 to improve a leak-barrier effect in the crotch region 8 of the chassis 2.

The core 47 of the body fluid absorbent panel 3 may be formed by fluff pulp or a mixture of fluff pulp and superabsorbent polymer particles. As the bottom sheet 48, liquid-impervious plastic film may be used. When the first sheet strip 31 and the second sheet strip 32 of the chassis 2 are formed from the continuous liquid-impervious sheet material, it is possible to omit the bottom sheet 48 from the body fluid absorbent panel 3. Stock materials for the wrapping sheet 49 may be selected from the group consisting of a liquid-pervious nonwoven fabric and a perforated plastic film.

It should be understood here that the first through fourth adhesive 41 through 44 are designated merely depending on the respective regions in which the adhesive is used but not depending on particular types of adhesive. More specifically, it is possible to use the one and same type of adhesive for the first adhesive 41 and the second adhesive 42 or it is possible to use the one and same type of adhesive for the second adhesive 42 and the third adhesive 43. As these first through fourth adhesive 41 through 44, it is possible to use hot melt adhesive which has conventionally been used in the relevant field of the art. Without departing the scope as well as the spirit of the present invention, bonding of the various members as the first through fourth adhesive 41 through 44 may be achieved using a welding technique such as heat-sealing or sonic-sealing technique.

Figure 5:
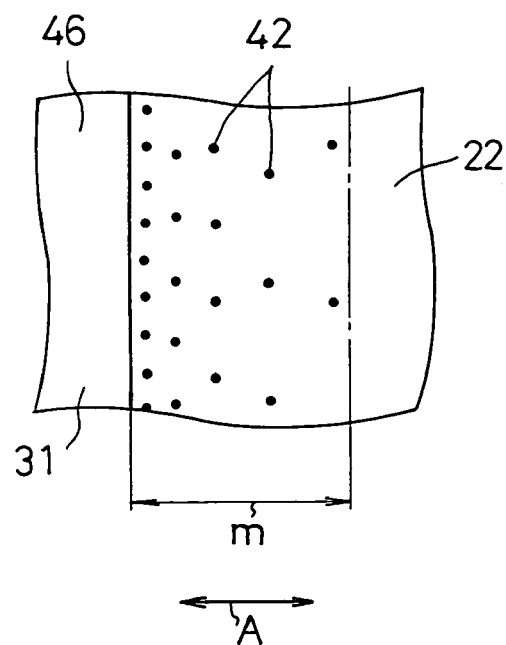
FIG. 5 is a scale-enlarged view showing a part of FIG. 2 to illustrate an example of adhesive layout.
Figure 6:
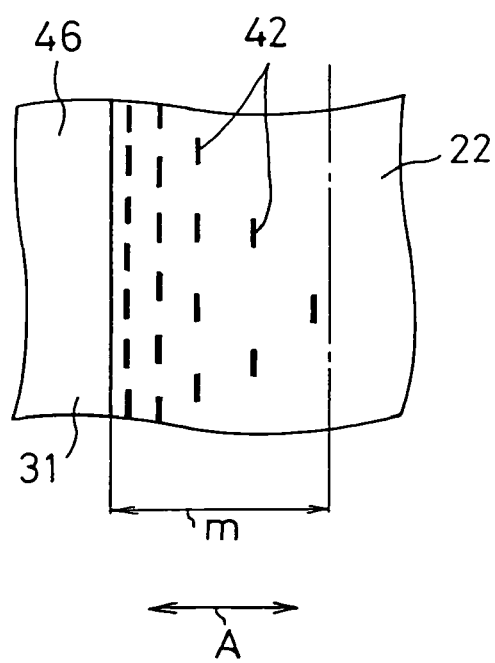
FIG. 6 is a view similar to FIG. 5.

FIGS. 5, 6 and 7 are scale-enlarged views showing a region P surrounded by an imaginary line in FIG. 2 to illustrate an example of layout according to which the second adhesive 42 is coated in the adjustably fixed region m intermittently in the transverse direction. In the case illustrated by FIG. 5, the second adhesive 42 is coated so as to form a plurality of dots. Distribution of these dots is densely distributed in the vicinity of the side edges 46 of the first sheet strip 31 and progressively becomes sparse as these dots get away from the side edges 46. In the case illustrated by FIG. 6, the second adhesive 42 is coated so as to form a plurality of short line segments. In these embodiments illustrated by FIGS. 5 and 6, the area ratio at which a plurality of dots occupy the unit area of the adjustably fixed region m is progressively reduced as these dots get away from the side edges 46. In the diaper 1 according to such embodiment, the stiffness of the chassis 2 which otherwise would become higher due to the presence of the bonding spots 51 can be gradually varied in the waist-surrounding direction so that the chassis 2 may become flexible as a whole. In the case illustrated by FIG. 7, the second adhesive 42 is coated so as to form a plurality of dots in substantially uniform distribution. Referring to FIGS. 5, 6 and 7, the outer sheet 21 and the inner sheet 22 are bonded to each other at the respective dots of the second adhesive 42 so as to form the bonding spots 51. It should be understood here that no particular shape is specified by the present invention and therefore the dots formed by the first through fourth adhesive 41 through 44 may be replaced, for example, by a spiral pattern obtained by coating hot melt adhesive using a spiral spray coater. In addition, the images 26 used as he display elements in the present invention may be replaced by a so-called indicator adapted to become visible when wetted with urine and to make the wearer's mother aware of occurrence of urination.

What is claimed is:

1. A disposable pull-on wearing article, comprising:
 a front waist region, a rear waist region, and a crotch region extending in a longitudinal direction of the article to connect the front and rear waist regions;
 said front and rear waist regions respectively having transversely opposite side margins bonded together so that said front and rear waist regions and crotch region cooperately define a pants-shaped configuration;
 said front and rear waist regions including a first sheet which is elastically stretchable in a waist-surrounding direction of said article and wherein said first sheet in at least one of said front and rear waist regions is provided on an inner surface thereof with a display element adapted to be visually recognizable from an outside of said article;
 said display element being formed on a sheet strip bonded to the inner surface of said first sheet by means of a first bonding arrangement; said sheet strip being interposed between said first sheet and a second sheet;
 said second sheet lying on an inner side of said wearing article behind said sheet strip and being elastically stretchable in said waist-surrounding direction;
 said first sheet being bonded to said second sheet by means of a second bonding arrangement in bonding zones extending outwardly in said waist-surrounding direction from side edges of said sheet strip towards spots at which said transversely opposite side margins of said front and rear waist regions are bonded together; and said second bonding arrangement comprising a plurality of bonding spots at which said first sheet and said second sheet are directly bonded to each other and which are arranged intermittently in said waist-surrounding direction as well as in the longitudinal direction of said wearing article orthogonal to said waist-surrounding direction;

wherein said bonding spots are located immediately adjacent the side edges of said sheet strip.

2. The wearing article according to claim 1, wherein said bonding spots are distributed in the bonding zones so that an area of said bonding spots per unit area of said inner surface is gradually reduced in said waist-surrounding direction away from the side edges of said sheet strip.

3. The wearing article according to claim 2, wherein
the bonding spots immediately adjacent the side edges of the sheet strip are inwardly spaced in the waist-surrounding direction from the respective spots, at which said transversely opposite side margins of said front and rear waist regions are bonded together, by respective bond-free zones in which the first and second sheets are free of direct attachment to one another.

4. The wearing article according to claim 1, wherein said bonding spots are formed only in said bonding zones which are defined within a range of about 10 to about 50 mm from said side edges of said sheet strip in said waist-surrounding direction.

5. The wearing article according to claim 1, wherein
said first sheet and said second sheet are formed from nonwoven fabric layers and a basis weight of said first sheet is a smaller than a basis weight of said second sheet; and
said first sheet has a luminous transmission of at least 55%.

6. The wearing article according to claim 5, wherein at least one of said first sheet and said second sheet contains elastomer fibers.

7. The wearing article according to claim 1, wherein,
among said front waist region, said rear waist region and said crotch region, at least said crotch region is provided on an inner surface of said second sheet with a body fluid absorbent panel including a body fluid absorbent core at least partially wrapped with a liquid-pervious sheet; and
a middle region of said body fluid absorbent panel as viewed in said waist-surrounding direction of said wearing article is bonded to said second sheet, whereas side regions of said body fluid absorbent panel as viewed in the waist-surrounding direction of said wearing article are free of direct attachment to said second sheet.

8. The wearing article according to claim 1, wherein
the bonding spots immediately adjacent the side edges of the sheet strip are inwardly spaced in the waist-surrounding direction from the respective spots, at which said transversely opposite side margins of said front and rear waist regions are bonded together, by respective bond-free zones in which the first and second sheets are free of direct attachment to one another.

9. The wearing article according to claim 1, wherein
the side edges of said sheet strip are bonded to the first sheet.

10. The wearing article according to claim 1, wherein
the sheet strip is non-stretchable in at least one of the waist-surrounding direction and the longitudinal direction.

11. The wearing article according to claim 1, wherein said bonding spots are distributed in the bonding zones so that a number of said bonding spots per unit area of said inner surface is gradually reduced in said waist-surrounding direction outwardly away from the side edges of said sheet strip.

12. The wearing article according to claim 1, wherein
said bonding spots comprise adhesive; and
in the bonding zones, a quantity of said adhesive per unit area of said inner surface is gradually reduced in said waist-surrounding direction outwardly away from the side edges of said sheet strip.

* * * * *